US008947237B2

(12) United States Patent
Margon et al.

(10) Patent No.: US 8,947,237 B2
(45) Date of Patent: Feb. 3, 2015

(54) PHYSIOLOGICAL DATA ACQUISITION UTILIZING VIBRATIONAL IDENTIFICATION

(75) Inventors: Kenneth Margon, Selangor (MY); Gubbi Umesh Renukanand, Selangor (MY)

(73) Assignee: Xanthia Global Limited (VG)

( * ) Notice: Subject to any disclaimer, the term of this patent is extended or adjusted under 35 U.S.C. 154(b) by 0 days.

(21) Appl. No.: 13/214,156

(22) Filed: Aug. 19, 2011

(65) Prior Publication Data
US 2012/0146795 A1 Jun. 14, 2012

Related U.S. Application Data

(63) Continuation-in-part of application No. 12/712,488, filed on Feb. 25, 2010.

(60) Provisional application No. 61/155,510, filed on Feb. 25, 2009, provisional application No. 61/179,605, filed on May 19, 2009.

(51) Int. Cl.
*G08B 23/00* (2006.01)
*H04B 3/36* (2006.01)
*G08B 21/00* (2006.01)
(Continued)

(52) U.S. Cl.
CPC .......... *A61B 5/0028* (2013.01); *G06F 19/3406* (2013.01); *A61B 5/002* (2013.01); *A61B 5/021* (2013.01); *A61B 5/0402* (2013.01); *A61B 5/05* (2013.01); *A61B 5/082* (2013.01); *A61B 5/11* (2013.01); *A61B 5/1117* (2013.01); *A61B 5/117* (2013.01); *A61B 5/14532* (2013.01); *A61B 5/14546* (2013.01); *A61B 5/14551* (2013.01);
(Continued)

(58) Field of Classification Search
CPC ...................................... A61N 1/365
USPC ................................. 600/509, 301
See application file for complete search history.

(56) References Cited

U.S. PATENT DOCUMENTS 5,458,123 A * 10/1995 Unger .......................... 600/509
6,740,033 B1 * 5/2004 Olejniczak et al. ........... 600/301
(Continued)

*Primary Examiner* — Jennifer Mehmood
*Assistant Examiner* — Pameshanand Mahase
(74) *Attorney, Agent, or Firm* — San Diego IP Law Group LLP

(57) ABSTRACT

The present invention utilizes an accelerometer (included within a wireless physiology monitoring device or as part of a separate device such as, but not limited to a smartphone, e.g., iPhone, or other mobile device) to link a patient with a separate medical data acquisition device such as a weight scale or a blood pressure monitor in order to collect and transmit a range of medical data associated with the user. The medical data acquisition device includes a vibration source for emitting a vibration at a predetermined or random frequency. When the acquisition device is activated, a vibration is transmitted from the through the patient and is detected by the accelerometer. The accelerometer then measures the particular frequency of vibration and transmits this information to a centralized monitoring unit (CMU). Based on the measured frequency, the CMU is able to know that the same patient wearing/holding the device is also the same patient using the data acquisition device. The vibration source may revolve through a number of predetermined frequencies (as determined on its own or instructed via the CMU) or simply generate a random frequency.

17 Claims, 5 Drawing Sheets

(51) Int. Cl.
  *G08B 19/02* (2006.01)
  *G08B 19/00* (2006.01)
  *A61B 5/05* (2006.01)
  *A61B 5/04* (2006.01)
  *A61B 5/00* (2006.01)
  *G06F 19/00* (2011.01)
  *A61B 5/021* (2006.01)
  *A61B 5/0402* (2006.01)
  *A61B 5/08* (2006.01)
  *A61B 5/11* (2006.01)
  *A61B 5/117* (2006.01)
  *A61B 5/145* (2006.01)
  *A61B 5/1455* (2006.01)

(52) U.S. Cl.
  CPC ....... *A61B 2562/0219* (2013.01); *G06F 19/322* (2013.01); *G06F 19/3418* (2013.01)
  USPC ............. 340/573.1; 340/407.1; 340/683; 340/582; 340/5.81; 340/407; 340/509; 340/547

(56) References Cited

U.S. PATENT DOCUMENTS

| | | | |
|---|---|---|---|
| 7,399,277 | B2 | 7/2008 | Saidara et al. |
| 2002/0055913 | A1 | 5/2002 | Rajan |
| 2002/0065466 | A1 | 5/2002 | Rather et al. |
| 2002/0067269 | A1* | 6/2002 | Cadell et al. ............... 340/573.1 |
| 2002/0109600 | A1 | 8/2002 | Mault et al. |
| 2007/0043597 | A1 | 2/2007 | Donaldson |
| 2007/0063850 | A1 | 3/2007 | Devaul et al. |
| 2007/0096927 | A1* | 5/2007 | Albert ....................... 340/573.1 |
| 2007/0247316 | A1* | 10/2007 | Wildman et al. .......... 340/572.4 |
| 2008/0001735 | A1 | 1/2008 | Tran |
| 2008/0119716 | A1 | 5/2008 | Boric-Lubecke et al. |
| 2008/0164999 | A1 | 7/2008 | Otto |
| 2008/0166028 | A1 | 7/2008 | Turek et al. |
| 2008/0175422 | A1 | 7/2008 | Kates |
| 2011/0196254 | A1* | 8/2011 | Wenzel et al. ............... 600/547 |

* cited by examiner

PHYSIOLOGICAL DATA ACQUISITION UTILIZING VIBRATIONAL IDENTIFICATION

CROSS-REFERENCE TO RELATED APPLICATIONS

This continuation-in-part application claims the benefit of U.S. patent application Ser. No. 12/712,488 and PCT/US10/253,325, both filed on Feb. 25, 2010, and both entitled "WIRELESS PHYSIOLOGY MONITOR," which claim priority under 35 U.S.C. §119(e) to U.S. Provisional Patent Application No. 61/155,510, entitled "WiFi OFDM Modulated Carrier for Heart and Lung Monitoring," filed Feb. 25, 2009, and U.S. Provisional Patent Application No. 61/179,605, entitled "Fall Detection and Heart/Lung Monitoring," filed May 19, 2009. The entireties of such applications are incorporated herein by reference.

BACKGROUND OF THE INVENTION

1. Field of Invention

The present invention relates to physiological measurement techniques and biotelemetry (i.e., medical telemetry), and more particularly to a system, device, and method for linking patient or device identifiers with medical test data through vibrational frequency magnitudes.

2. Description of Related Art

Several technologies have been developed to help doctors and medical professionals access, visualize, or learn more about a patient's internal organs without having to undertake an invasive medical procedure.

For example, an electrocardiogram (an "EKG") can be used to determine information about a patient's heart. Electrical waves generated by the heart are measured by electrodes that are placed on the skin of a patient. The voltage between the electrodes is displayed on a monitor for analysis of the patient's heart. EKGs have several disadvantages, however. The electrodes must be physically connected to the patient being monitored, which can be bothersome to the patient, for the duration of the EKG test. In addition, an EKG does not produce an image of the heart itself and is not a direct measurement of the motion of the heart. Therefore, the detected electrical characteristics are merely analogues of the heart's motion.

Computer axial tomography ("CAT" or "CT") scans can be used to generate three-dimensional (3D) images of a human body. CT scanners emit a fan-shaped x-ray beam, which passes through a patient's body before being detected by rotating source detectors. Depending on the type of tissue the x-rays pass through, the x-rays will be attenuated or will pass through unimpeded. The x-rays that pass through the body are detected and used to generate an image of the tissues exposed to the x-rays. Images of internal organs can therefore be generated. Yet, CT scanners suffer from numerous disadvantages. They are expensive, bulky and immobile, require patients to remain generally immobile for extended periods of time during the scanning, and expose patients to potentially harmful x-rays.

Magnetic resonance imaging ("MRI") scanners can be used to generate images of a human body. An MRI scanner uses magnetic fields to align the nuclear magnetization of hydrogen atoms in the body. The magnetization of these atoms is then altered to produce a magnetic field, which is detected by the scanner and used to generate an image. As with CT scanners, MRI scanners are expensive, very large and immobile, and require patients to remain relatively immobile during the procedure. Furthermore, MRI scanners cannot be used by some people with metal implants.

SUMMARY OF THE INVENTION

The system comprises a plurality of wireless electronic devices and a server. The wireless electronic devices include a device having an accelerometer and a medical data acquisition device having a vibration source. In one embodiment, the server comprises an application. In another embodiment, the application is located on one of the wireless electronic devices (e.g., the device having the accelerometer). The application and wireless electronic devices can be connected through a wireless interface and a gateway.

The device having the accelerometer can include a pendant, a cell phone, a wrist watch, a hospital bed, etc. The data acquisition device can include a scale, blood pressure device, a floor mat, a car seat, etc. The server can include hardware, software, firmware, etc. The wireless interface can include Wifi, Bluetooth, etc. The gateway may be an independent device or may be contained in one of the wireless electronic devices (e.g., the device having the accelerometer).

The data acquisition device can assign its own vibration frequency or be assigned a vibration frequency by the application located in the server or the device having the accelerometer. When the data acquisition device assigns its own vibration frequency, the data acquisition device must transmit that frequency along with other data transmitted to the server. The transmitted data can be a patient's personal data records. When the application is located in the server and assigns the vibration frequency to the data acquisition device, the transmitted data to the server does not need to include the vibration frequency, as the server already knows the vibration frequency. The assigned frequency chosen should be unique, and not a typical frequency used by common electrical or mechanical devices, such as multiples of 50 or 60 Hz. In one embodiment, the assigned frequencies are prime numbers.

In one embodiment, the device having the accelerometer is uniquely associated with a particular person at a selected frequency, whereas the data acquisition device is not uniquely associated with the particular person. The data acquisition device is assigned a selected frequency. The selected frequency is able to be transmitted mechanically through a medium, such as a person or animal (e.g., a dog), from the data acquisition device to the device having the accelerometer. When the data acquisition device is activated, it vibrates at the selected frequency. At the same time, the data acquisition device transmits data (e.g., measured medical data) through the gateway to the server and transmits the selected frequency to the device having the accelerometer. The device having the accelerometer transmits data (e.g., personal data record, the selected frequency, etc.) to the server as well. The server matches up the data from the data acquisition device and the data from the device having the accelerometer, based on matching frequencies. By matching the data from these two devices, the measured data from the data acquisition device which was not associated with a particular person, can now be associated with the data record for that particular person.

In another embodiment, the scenario is reversed, and the data acquisition device having the vibration source is uniquely associated with a particular person at a selected frequency, and the device having the accelerometer is not uniquely associated with a particular person. In this embodiment, the device having the accelerometer reports the received frequency back to the application on the server, and the server again matches up the data based on frequency, such that the device which was not associated with a particular person, can now be associated with the data for that particular person. In another embodiment, each of the wireless devices has an accelerometer.

The foregoing, and other features and advantages of the invention, will be apparent from the following, more particular description of the preferred embodiments of the invention, the accompanying drawings, and the claims.

BRIEF DESCRIPTION OF THE DRAWINGS

For a more complete understanding of the present invention, the objects and advantages thereof, reference is now made to the following descriptions taken in connection with the accompanying drawings in which.

DETAILED DESCRIPTION OF EMBODIMENTS

Figure 1:
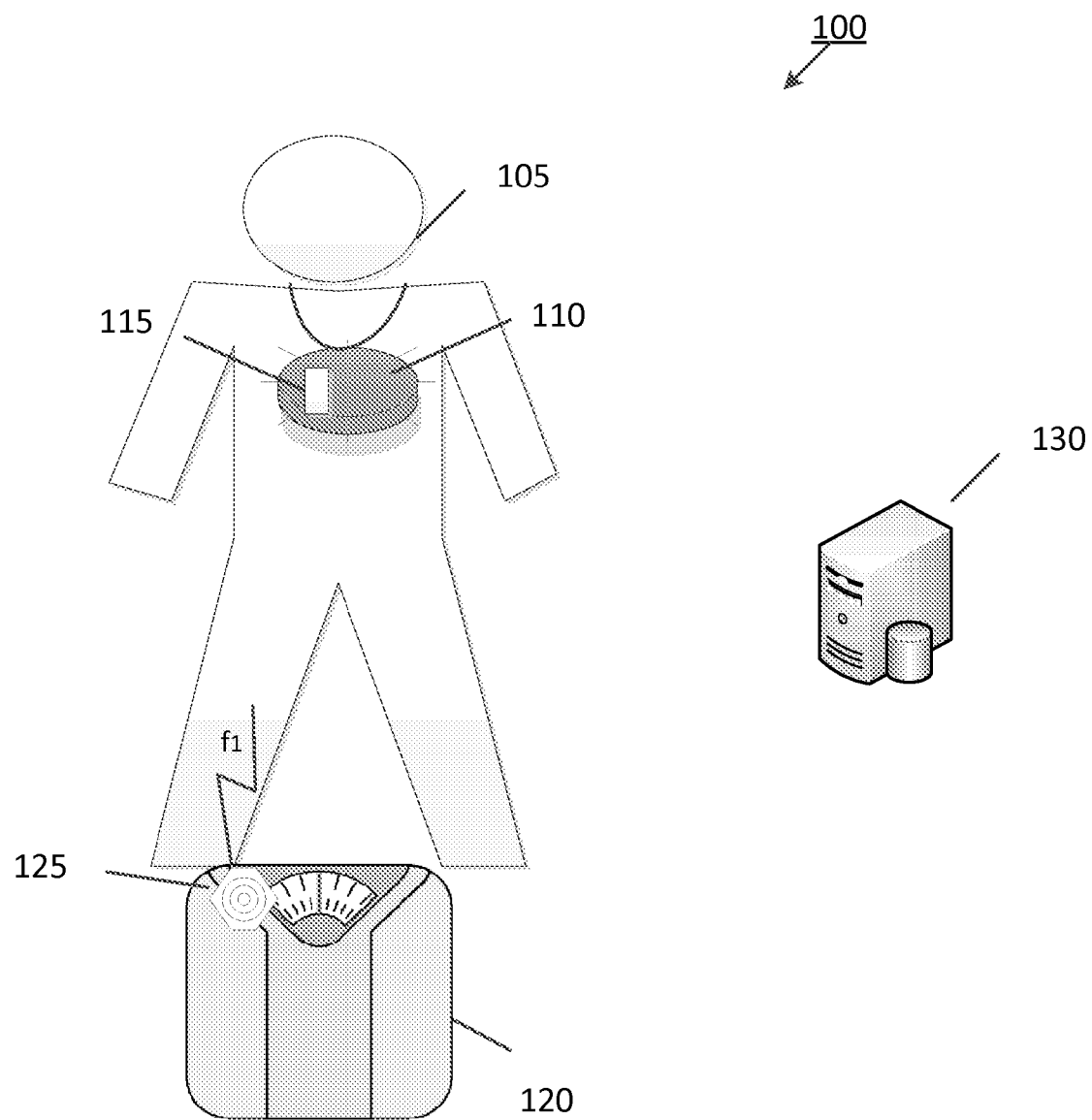
FIG. 1 illustrates medical test system for linking a user, e.g., a patient, to a medical device (and thus, medical test results) according to an embodiment of the invention.

Further features and advantages of the invention, as well as the structure and operation of various embodiments of the invention, are described in detail below with reference to the accompanying FIGS. 1-5, wherein like reference numerals refer to like elements.

U.S. patent application Ser. No. 12/712,488, entitled "Wireless Physiology Monitor," the entire disclosure of which is incorporated by reference herein, describes a new non-invasive technique for physiology monitoring and assessment implemented by, for example, a wireless physiology monitoring device. Particularly, a patient is subjected to a non-harmful and relatively low power electromagnetic RF source diagnostic signal normally associated with a communications protocol such as, but not limited to a version of the IEEE 802.11(x) family of protocols in the 2.4, 3.6, or 5 GHz spectrum bands. The source diagnostic signal could be generated by the wireless physiology monitoring device itself or taken from background radiation generated from external sources such as, but not limited to, a wireless router or Internet access point. In lay terms, that source diagnostic signal undergoes modification as it passes through the medium of the patient due to absorption, reflection, scattering, etc., the precise physics of which are readily understood by one of ordinary skill in the art. After passing through the patient, the modified signal is acquired and compared to the original source signal. The differences between the source and modified signals are then analyzed to monitor essential and typical life processes, activities, and functions such as, but not limited to measuring heart rate and detecting heart defects, and respiratory rate. For example, using Doppler Effect principles, heart rate and motion can be measured from the differences in frequency, phase, and/or wavelength between the source signal and the modified signal reflected back from the heart moving within the patient. Further specifics of the wireless physiology monitoring device and the techniques implemented by such can be found in the '488 application.

The wireless physiology monitoring device can take any form factor. In one embodiment of the invention, the device is a standalone hand-held device for optimum portability. For example, the device may take the form of a pendant, which may be worn around a patient's neck. In another embodiment of the invention, the device can be included as a component within a multi-purpose mobile device such as, but not limited to a cell phone, a laptop computer, a personal digital assistant (PDA) or smart-phone, e.g., Blackberry, PALM, Android, iPhone, and the like. In yet another embodiment of the invention, the device is included as a component within a relatively immobile device such as a desktop computer or wireless router such as the network node. Alternatively, the device may be included as a part of a larger apparatus such as a hospital bed, gurney, or any type of equipment where a patient may be located or adjacent thereto. The device may further include a biometric sensor (not shown) for identifying the individual using the device. For example, the device may optionally include a fingerprint scanner, retinal scanner, or other biometric scanner, the identification and implementation of which is apparent to one of ordinary skill in the art.

As further described in the '488 application, the device may comprise a means for motion detection such as, but not limited to a 3-axis accelerometer or the like, the identification and implementation of which is apparent to one of ordinary skill in the art. Motion detection generally refers to the ability to sense whether a human has moved and if so, the direction and magnitude of such movement at any given instant in time. This includes "fall detection," which refers to a patient such as an elderly user of the device having fallen or moved suddenly and perhaps harmfully due to, for example, an accident or syncope, which is a partial or complete loss of consciousness and posture.

In operation, once a fall or other irregular movement is detected by the accelerometer, the device may begin monitoring and preferably recording—either locally or remotely by a central monitoring unit (CMU), e.g., a server and/or database located on the Internet or a private internal network—various functions of the patient's heart and lungs. In other words, a fall may trigger the operation of the device and the physiological data gathered by the device can be transmitted in real-time to the CMU to convey the data as well as the occurrence of the fall itself to a medical provider or health care professional.

The present invention utilizes an accelerometer (included within the wireless physiology monitoring device noted above or as part of a separate device such as, but not limited to a smartphone, e.g., iPhone, or other mobile device) to link a user, e.g., patient, with a separate medical data acquisition device such as, but not limited to a weight scale or a blood pressure monitor in order to collect and transmit a range of medical data associated with the user. The use of a weight scale or a blood pressure monitor is exemplary only and one of ordinary skill in the art recognizes that any one of numerous types of data acquisition devices may be implemented. In the case of a weight scale, the weight scale includes a vibration source for emitting a vibration at a predetermined or random frequency. When a patient steps onto the weight scale while simultaneously wearing or holding a device including the accelerometer, the vibration is transmitted from the weight scale, through the patient, and is detected by the accelerometer. The accelerometer then measures the particular frequency of vibration and transmits this information via the device to the CMU, which is also in communication with the scale as well (i.e., the CMU receives, from the scale, a frequency value that was generated by the scale). Based on the measured frequency, the CMU is able to know that the same patient wearing/holding the device is also the same patient being weighed and is thus able to store, among other things, the weight measured by the scale, an identity of either the patient or the device worn/held by the patient at the time, the time of the measurement, additional physiology data measured by the wireless physiology monitoring device, or any combination/subset thereof, into a record associated with the particular patient. Each time the data acquisition device, e.g., weight scale, is activated, it will generate a different frequency. For example, the vibration source may revolve through a number of predetermined frequencies (as determined on its own or instructed via the CMU) or simply generate a random frequency. Such an identification/monitoring system is particularly useful where multiple users are using the accelerometer device and/or the data acquisition device.

The following example is provided to better illustrate the above acquisition technique. The weight scale receives a magnitude of a vibration frequency from the CMU of 57 Hz. The patient wearing the wireless physiology monitoring device steps on the scale, which vibrates at 57 Hz at some point. The device detects the vibration of 57 Hz and transmits this to the CMU. The CMU then knows that the particular scale, which vibrated at 57 Hz, is weighing the same patient wearing the device, which detected the 57 Hz. Both weight data and physiology data acquired by the device are associated with one another and the corresponding patient—this information can then be stored into a respective electronic medical record associated with the patient. If the device further includes a biometric sensor, the CMU is able to acquire the respective biometric information sensed and determine the identity of the patient if the appropriate corresponding biometric record of that patient already exists.

Prior to a subsequent use, the scale switches to a different vibration frequency such as 61 Hz. A second patient (using the same device as the first patient was using or a different device) then steps on the scale and is vibrated at 61 Hz, which is detected by the accelerometer of the worn device. The CMU is then able to determine that the second patient's weight from the scale should be associated with the information acquired from the device being worn by the patient at that time. One of ordinary skill in the art recognizes that numerous permutations exist on the above technique for acquiring medical data from other medical devices used in connection with the device. For example, as described above, the medical device, e.g., scale, blood pressure monitor, oximeter, breath analyzer, etc., may request the CMU to identify a particular vibration frequency. In another example, the medical device may select a vibration frequency and transmit the magnitude of the known frequency to the CMU rather than requesting it. The medical device may change vibration frequencies at predetermined intervals—after every 30 or 60 seconds the medical device switches to a new frequency.

FIG. 1 illustrates medical test system 100 for linking a user, e.g., a patient 105, to a medical device (and thus, medical test results) according to an embodiment of the invention. Particularly, the system 100 comprises a device 110, which could be worn by the patient 105, e.g., via a necklace (as shown), or held by hand, and a medical data acquisition device 120. The device 110 comprises an accelerometer 115 or other suitable detection component, the identification and implementation of which is apparent to one of ordinary skill in the art, for measuring vibrational frequencies. The device 110 further includes a communications transceiver (not shown), the identification and implementation of which is apparent to one of ordinary skill in the art, for conveying data to and from the device 110. In an embodiment of the invention, the device 110 further includes physiology monitoring circuitry as described in U.S. patent application Ser. No. 12/712,488. The medical data acquisition device 120 comprises a vibrational source 125 and a communications transceiver (not shown). The medical data acquisition device 120 may be a weight scale as shown. The vibrational source 125 is capable of generating a vibration at different frequencies. The communications transceiver with the medical data acquisition device 120 may be any type of communications transceiver, the identification and implementation of which is apparent to one ordinary skill in the art. The system 100 may further include an optional server and/or database 130 (CMU), which is able to communicate with the device 110 and the medical data acquisition device 120 though conventional communications protocols, the identification and implementation of which is apparent to one of ordinary skill in the art.

The patient 105 can be a human or animal (living or deceased), or any other test subject. The device 110 is shown hanging from a necklace, but can be any type of device either worn, e.g., a wristband, or held by the patient. In the case of a posthumous test subject, the device 110 can be placed on or connected to the subject through conventional means, the identification and implementation of which is apparent to one of ordinary skill in the art.

In operation, the vibrational source 125 generates a vibration at a first frequency, $f_1$. The vibration may be commenced upon activation of the medical data acquisition device 120 or upon receiving an instruction received from the device 110 or the server 130. The first frequency is transmitted through the patient's body and is detected by the accelerometer 115. The accelerometer 115 determines the magnitude of the first frequency and communicates the magnitude to the server 130 via the device 110. In the communication of the frequency magnitude, the device 110 may add additional data along with the magnitude such as, but not limited to, physiology data pertaining to the test subject, time/date, location information, and a unique device ID or patient ID.

The medical data acquisition device 120 communicates to the server 130 medical test data, e.g., weight, acquired at the time of the test. In the case where the server 130 does not know beforehand the magnitude of the first frequency, the medical data acquisition device 120 transmits such to the server 130. Additionally, the medical data acquisition device 120 may add additional data along with medical test data such as, but not limited to time/date, location information, and a unique device ID.

Upon receiving the information from the device 110 and the medical data acquisition device 120, the server 130 creates and/or stores a record of the received information linking the patient 105 (directly or indirectly through the device ID of the device 110) with the medical data received from the medical data acquisition device 120. The record may include information such as, but not limited, vibration frequency, time/date, location information, unique device ID of device 110, unique device ID of acquisition device 120, medical data (e.g., physiological data) generated by device 110, medical data (e.g., weight) generated by the acquisition device 120, patient ID, or any combination/subset thereof. The server 130 may utilize an automated algorithm to link the information from the device 110 and the information medical acquisition device 120 by utilizing the magnitude of the first frequency or alternatively time/date and/or location information.

Figure 2:
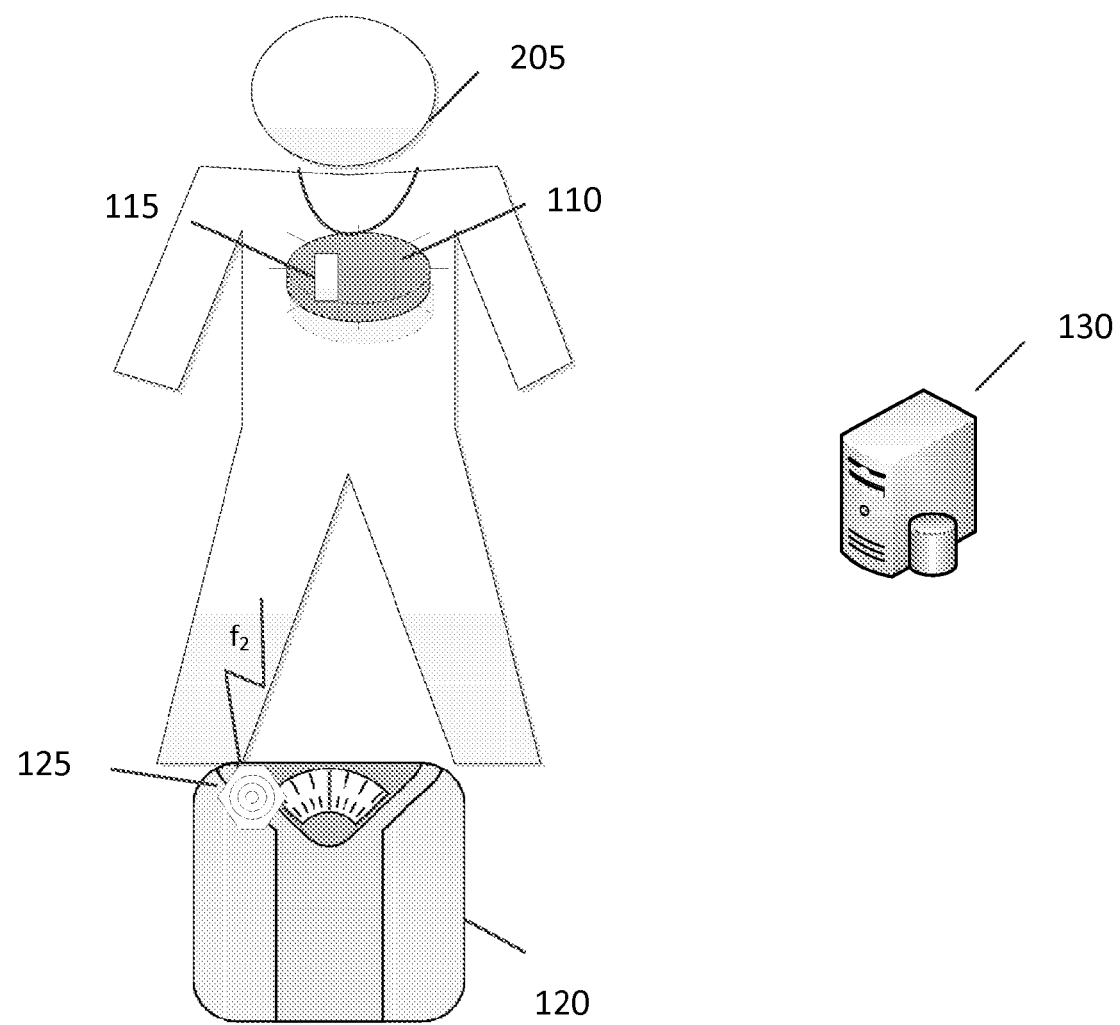
FIG. 2 illustrates a subsequent use of the system of FIG. 1 by a patient.

FIG. 2 illustrates a subsequent use of the system 100 by a patient 205. Particularly, upon a subsequent activation of the medical data acquisition device 120, the vibration source 125 generates a vibration at a second frequency, $f_2$. The patient 205 may be different than the patient 105, or patient 205 may be the same person as patient 105, but performing another test. Like the first frequency, the magnitude of the second frequency may be received from the server 130 or determined by the acquisition device 120 itself. The second frequency is transmitted from the acquisition device 120 to the device 110 by vibrating the patient 205. The accelerometer 115 determines the magnitude of the frequency and transmits such, along with optional additional information as noted above, to the server 130. The process can be repeated on numerous occasions by numerous patients.

The vibrational frequencies (e.g., the first and second vibrational frequency) are ideally unique. In other words, the vibrational frequencies do not overlap commonly used frequencies implemented by other devices such as wireless electronics. In a preferred embodiment, the vibrational frequencies are prime numbers. Prime numbers include, for example, 2, 3, 5, 7, 11, 13, 17, 19, 23, 29, 31, 37, 41, 43, 47, 53, 59, 61, 67, 71, 73, 79, 83, 89, 97, etc. In another embodiment, the vibrational frequencies are less than 20 KHz.

Figure 3:
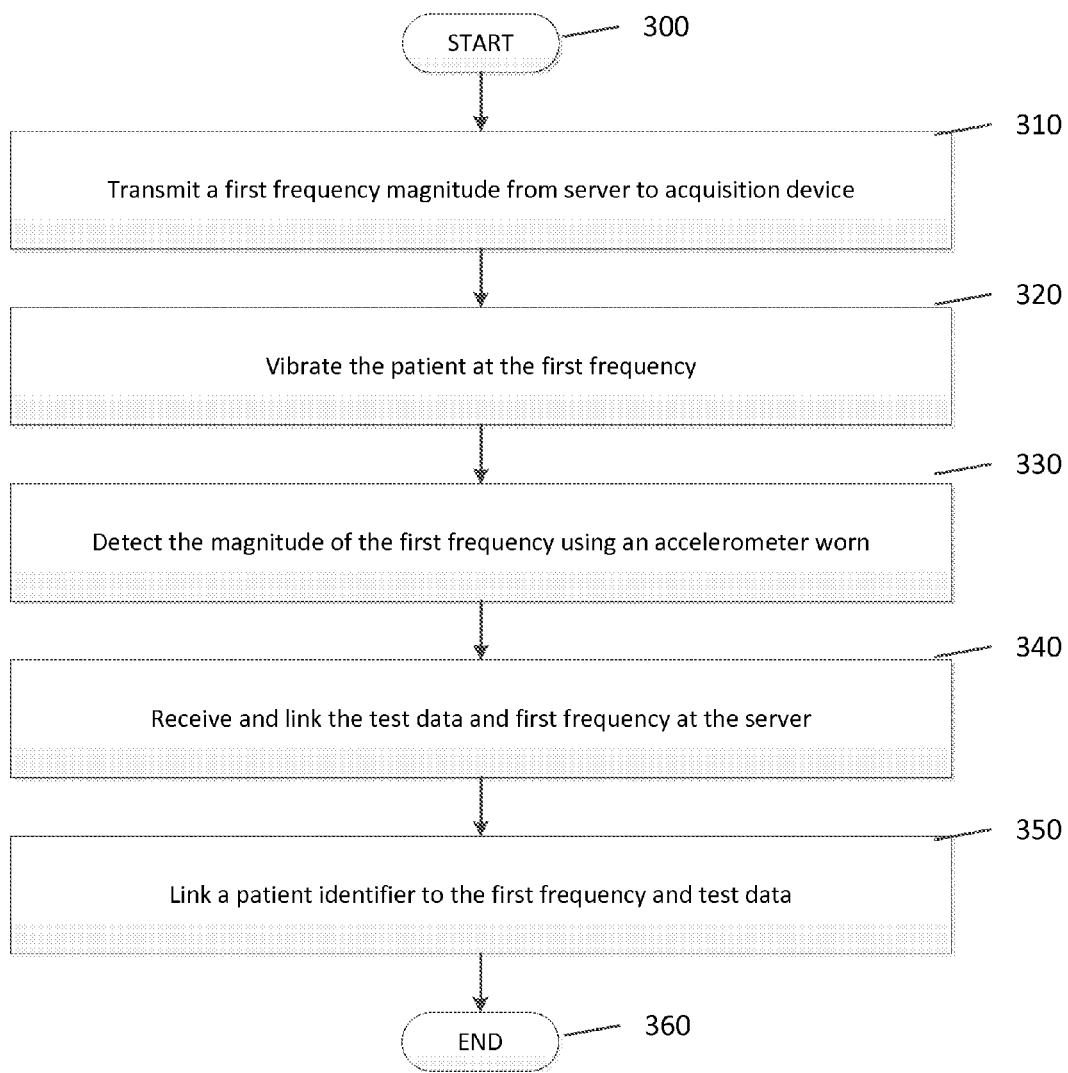
FIG. 3 illustrates a method for linking a patient to test results using a vibrational frequency according to an embodiment of the invention.

FIG. 3 illustrates a method 300 for linking a patient to test results using a vibrational frequency according to an embodiment of the invention. At step 310, the server 130 transmits a first frequency magnitude to the data acquisition device 120. Next, at step 320, the acquisition device 120 vibrates the patient 105 at the first frequency. The accelerometer 115 associated with the patient 105 detects and measures the magnitude of the first frequency at step 330. At step 340, the server 130 receives the test data from the acquisition device 120 and the first frequency from the device 110, as well as additional information as noted above, and links the test data to the first frequency. Next, at step 350, a patient identifier (or device 110 identifier) is linked to the first frequency and test data. The process ends at step 360.

Figure 4:
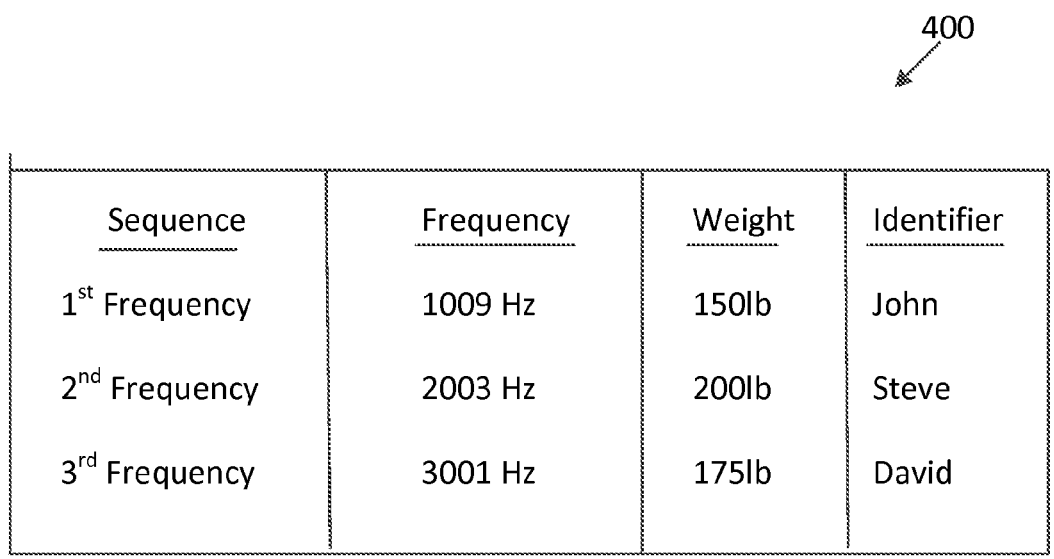
FIG. 4 illustrates an exemplary database of patients' records according to an embodiment of the invention.

FIG. 4 illustrates an exemplary database 400 of patients' records according to an embodiment of the invention. Particularly, the first column shows the order of frequencies provided used by the acquisition device 120. This sequence may also contain a time stamp or location identifying information. The second column contains unique frequencies 1,009 Hz, 2,003 Hz, and 3,001 Hz, each of which are prime numbers. The third column shows test data, e.g., weights, measured by the acquisition device. The fourth column shows first names as an example of patient identifiers (alternatively, unique device IDS could be used, among others identifiers). The database 400 provides a sequence for each patient, providing a frequency like time stamp.

Figure 5:
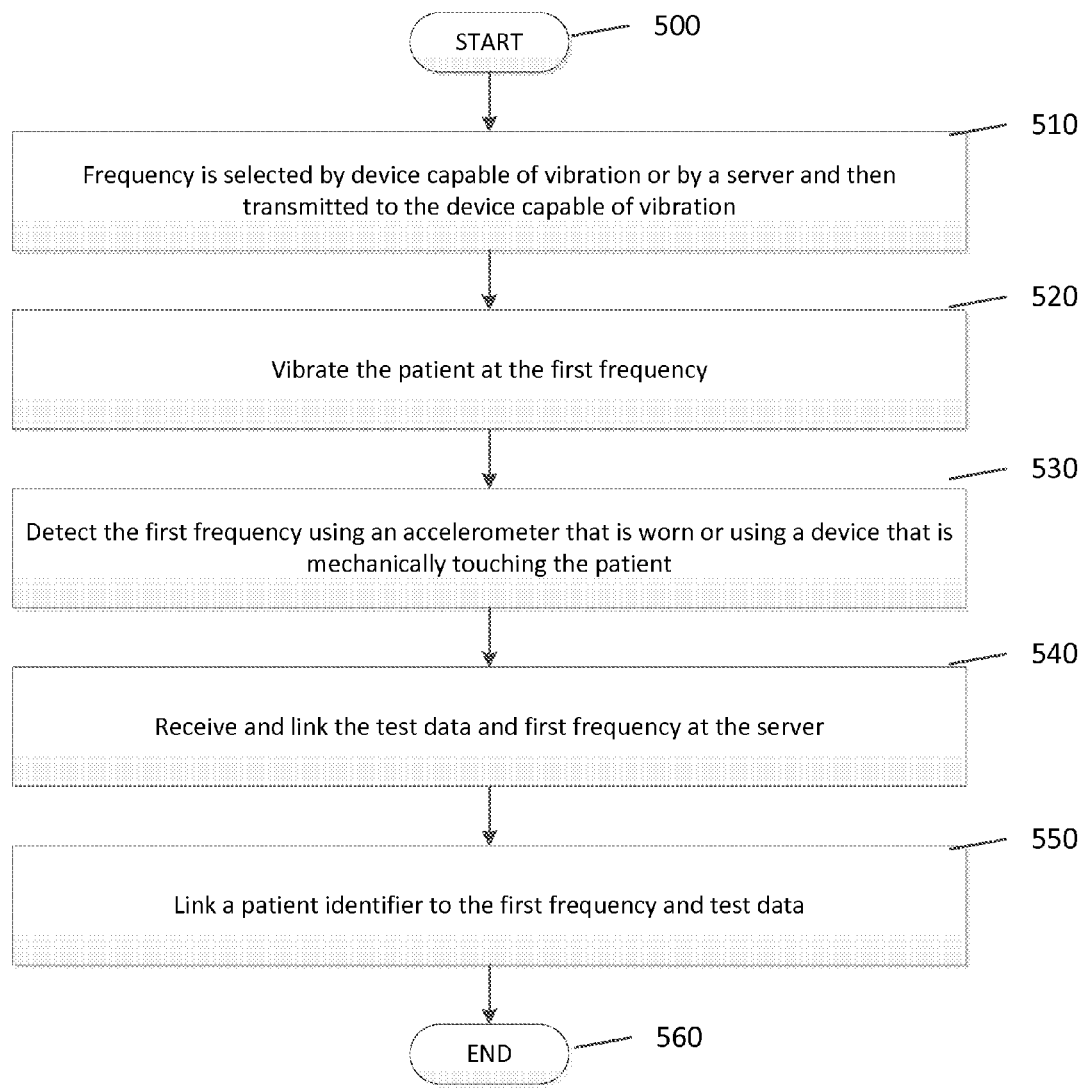
FIG. 5 illustrates a flow chart of a process of linking a patient to test results according to an embodiment of the invention.

FIG. 5 illustrates a flow chart of a process of linking a patient to test results. The process starts at 500. At step 510, frequency is selected by the device 120 capable of vibration or by the server 130 and then transmitted to the device 120 capable of vibration. Next, at step 520, the data acquisition device 120 vibrates the patient 105 at the first frequency. The magnitude of the first frequency is detected at step 530. The detection can be by an accelerometer that is worn or using the device 110 that is mechanically touching the patient, such as a hospital bed. At step 540, the server 130 receives and links the test data and first frequency. Next, at step 550, the process links a patient identifier to the first frequency and test data. The patient identifier can be associated with the device 110 or the patient identifier can be manually entered into a patient's electronic record. The process ends at step 560.

Although the invention has been described in the context of a human patient, the inventive concepts described herein can be used on any type of living subject including animals. For example, the inventive concepts can be implemented in veterinarian applications where medical information is sought for animals such as dogs and cats. The device 110 may implemented as part of a collar or harness worn by the animal.

The communications transceivers noted above may implement one or more communications protocols such as, but not limited to, various flavors of the IEEE 802 set of protocols (sometimes referred to as "WiFi"), Bluetooth, Zigbee, or wired Ethernet, the implementation of which are apparent to one of ordinary skill in the art. Device 110 and acquisition device 120 may communicate with the server via the Internet or a local access network comprising intermediate communication nodes.

Again the use of weight scale is exemplary only and other types of medical data acquisition devices may be used including without limitation, glucose monitor; a blood pressure monitor; a blood alcohol monitor; breath analyzer; drug detection instrument; coagulation monitor or instrument; pulse oximeter; electrocardiogram (EKG or ECG) machine; echocardiogram machine; nuclear magnetic resonance (NMR) imaging machine, computerized axial tomography (CAT) scanner; ultrasound imaging machine; point-of-care test instruments for measuring acute disease markers or disease risk markers; point-of-care instruments for measuring infectious disease markers; point-of-care genetic or genotyping test instruments for measuring genetic sequences of mutations for infectious diseases, cancer, drug susceptibility, drug resistance, drug metabolism efficacy or disease risk; diabetes monitoring instruments that measure glucose and/or hemoglobin A1c; point-of-care test instruments for measuring women's health and fertility markers; point of care test instruments for measuring cancer markers; point-of-care instruments for measuring the comprehensive metabolic panel, including any or all of glucose, calcium, albumin, total protein, sodium, potassium, carbon dioxide or bicarbonate, chloride, blood urea nitrogen, creatinine, alkaline phosphatase, alanine aminotransferase, aspartate aminotransferase, bilirubin; and point-of-care hematology analyzers for measuring, among other parameters, red blood cell (RBC) count, white blood cell count, platelet count, platelet volume, leukocyte differential count and/or proportion, hemoglobin, hematocrit, RBC volume, RBC hemoglobin, erythrocyte sedimentation rate, and reticulocyte count.

In accordance with some embodiments, the various aspects described above may be implemented using computer programming or engineering techniques including computer software, firmware, hardware or any combination or subset thereof. Any resulting program, having computer-readable code means, may be embodied or provided within one or more computer-readable media, thereby making a computer program product, i.e., an article of manufacture, according to the invention. The computer readable media may be, for instance, a fixed (hard) drive, diskette, optical disk, magnetic tape, semiconductor memory such as read-only memory (ROM), etc., or any transmitting/receiving medium such as the Internet or other communication network or link. The article of manufacture containing the computer code may be made and/or used by executing the code directly from one medium, by copying the code from one medium to another medium, or by transmitting the code over a network. In addition, one of ordinary skill in the art of computer science will be able to combine the software created as described with appropriate general purpose or special purpose computer hardware, Personal Digital Assistant (PDA) hardware, cellular telephone hardware or other electronic hardware to create a computer system or computer sub-system embodying the method of the invention. One of ordinary skill in the art will understand that the various embodiments can also be implemented on circuitry, which, as defined herein, can be any combination of general purpose hardware, software, firmware, and/or special purpose hardware, including, but not limited to, a central processing unit, FPGA, ASIC or other known devices.

The invention has been described herein using specific embodiments for the purposes of illustration only. It will be readily apparent to one of ordinary skill in the art, however, that the principles of the invention can be embodied in other ways. Therefore, the invention should not be regarded as being limited in scope to the specific embodiments disclosed herein.

The invention claimed is:

1. A system comprising:
    a device having an accelerometer and a patient identifier associated with a particular patient record, wherein the accelerometer is configured to detect a frequency of a mechanical vibration of a patient;
    a data acquisition device configured to measure patient data, the data acquisition device having a mechanical vibration source to mechanically vibrate the data acquisition device and the patient at a pre-selected vibrational frequency less than radio frequency; and
    a server configured to receive the patient identifier, the patient data, and the pre-selected vibrational frequency, the server configured to match up the patient identifier with the patient data based on the pre-selected vibrational frequency.

2. The system of claim 1, wherein the pre-selected vibrational frequency is less than 3 kilohertz.

3. The system of claim 2, wherein the pre-selected vibrational frequency is a prime number.

4. The system of claim 2, wherein the pre-selected vibrational frequency is a patient identifier.

5. The system of claim 1, wherein the patient data is included into the particular patient record.

6. The system of claim 4, wherein the pre-selected vibrational frequency is associated with only one patient.

7. The system of claim 1, wherein the data acquisition device comprises an antenna configured to receive an identifier of the pre-selected vibrational frequency from the server.

8. The system of claim 7, wherein the antenna provides test results to the server.

9. A method implemented on one or more processors, the method comprising:
    associating a patient identifier with a particular patient record;
    measuring patient data using a data acquisition device;
    mechanically vibrating the data acquisition device and the patient at a pre-selected vibrational frequency less than 3 kilohertz;
    detecting the pre-selected vibrational frequency of the patient; and
    matching up the patient identifier with the patient data based on the pre-selected vibrational frequency.

10. A device comprising:
    an accelerometer configured to detect a pre-selected mechanical vibrational frequency of a patient and corresponding to measured patient data and associated with the patient having a patient identifier, wherein the pre-selected mechanical vibrational frequency is less than 3 kilohertz; and
    a transceiver configured to receive the magnitude of the pre-selected mechanical vibrational frequency and transmit the patient identifier, wherein the patient identifier is matched up with the patient data based on the pre-selected mechanical vibrational frequency.

11. The system of claim 10, wherein the device comprises a smartphone, an iPhone, or a pendant.

12. A device comprising:
    an application configured to select a predetermined vibrational frequency, wherein the predetermined vibrational frequency is less that 3 kilohertz;
    a mechanical vibration source for producing the predetermined vibrational frequency and mechanically vibrate the device and a patient at the predetermined vibrational frequency;
    medical test circuitry configured to measure patient data corresponding to the patient; and
    a transceiver configured to transmit an identifier of the predetermined vibrational frequency and the measured patient data, wherein the measured patient data is matched up with the patient based on the predetermined vibrational frequency.

13. The device of claim 12, wherein the device comprises a data acquisition device.

14. The device of claim 12, wherein the predetermined vibrational frequency is a prime number.

15. A device comprising:
    an application configured to select a predetermined mechanical vibrational frequency to be used on a patient, wherein the predetermined mechanical vibrational frequency is less than 3 kilohertz;
    a transceiver configured to receive patient data and a patient identifier; and
    matching circuitry configured to match the patient data and the patient identifier based on the predetermined mechanical vibrational frequency.

16. The device of claim 15, wherein the device comprises a server.

17. The device of claim 15, wherein the predetermined mechanical vibrational frequency is a prime number.

* * * * *